United States Patent [19]

Szur

[11] 4,049,668
[45] Sept. 20, 1977

[54] CATIONIC FLUOROCHEMICAL SURFACTANTS

[75] Inventor: Alex J. Szur, North Plainfield, N.J.

[73] Assignee: Diamond Shamrock Corporation, Cleveland, Ohio

[21] Appl. No.: 560,697

[22] Filed: Mar. 21, 1975

[51] Int. Cl.$^2$ ........................................... C07D 213/20
[52] U.S. Cl. ............................. 260/295 R; 260/78 R; 428/474
[58] Field of Search ................................... 260/295 R

[56] References Cited

U.S. PATENT DOCUMENTS

| | | | |
|---|---|---|---|
| 3,042,642 | 7/1962 | DeMarco et al. | 260/29.6 |
| 3,350,218 | 10/1967 | Gagliardi | 428/274 |
| 3,510,494 | 5/1970 | Gagliardi | 260/295 |

Primary Examiner—Norman A. Drezin
Attorney, Agent, or Firm—Neal T. Levin; Leslie G. Nunn

[57] ABSTRACT

Cationic fluorochemical surfactants useful as antistatic agents and lubricants for polymeric shapes are prepared from 2,2,3,4,4,4-hexafluorobutanol or perfluorobutyric acid. Hexafluorobutanol is reacted with bromoundecanoic acid to obtain a bromoester which is then reacted with pyridine to obtain a cationic surfactant. Perfluorobutyric acid is esterified with methanol to obtain methyl perfluorobutyrate which is then reacted with dimethylaminopropylamine to obtain an aminoamide which is then reacted with hydrogen peroxide to obtain the N-oxide derivative which is neutralized with glycolic acid to obtain a cationic surfactant, a salt of the N-oxide derivative.

3 Claims, No Drawings

CATIONIC FLUOROCHEMICAL SURFACTANTS

BACKGROUND OF THE INVENTION

1. Field of the Invention

This invention relates to cationic fluorochemical surfactants useful as antistatic agents and lubricants for polymeric shapes.

2. Description of the Prior Art

U.S. Pat. No. 3,042,642 — De Marco et al., issued July 3, 1962, describes use of a mixture of a quaternary pyridinium compound and an aqueous perfluoroalkyl acrylate to render textiles water-resistant and oil-resistant.

U.S. Pat. No. 3,350,218 — Gagliardi, issued Oct. 31, 1967, describes "soilproofing" textiles with quaternary ammonium compounds derivatives of highly fluorinated aliphatic carboxylic acids.

U.S. Pat. No. 3,510,494 — Gagliardi, issued May 5, 1970, describes soilproofing of textiles with highly fluorinated quaternary ammonium compounds containing carboxamido, thioether and acid linkages between fluoro moiety and the quaternized nitrogen.

Although these patents teach preparation of fluorinated surfactants, there is a definite need for improved fluorinated surfactants having useful properties as antistatic agents and lubricants for polymeric shapes.

STATEMENT OF THE INVENTION

Fluorochemical cationic surfactants are prepared:

A. by reaction of 2,2,3,4,4,4-hexafluorobutanol with bromoundecanoic acid to obtain the corresponding bromester which is then reacted with pyridine to obtain a pyridinium bromide salt, and B. by esterification of perfluorobutyric acid with methanol to obtain methyl perfluorobutyrate which is reacted with 3-dimethylaminopropylamine to obtain an aminoamide reaction product which is then reacted with hydrogen peroxide to obtain the corresponding N-oxide reaction product which is then neutralized with glycolic acid to obtain a salt of the N-oxide reaction product. Both salts are cationic surfactants which are useful as antistatic agents and lubricants for polymeric shapes such as nylon film and fibers.

DESCRIPTION OF THE PREFERRED EMBODIMENTS

The fluorochemical surfactants of the present invention are cationic surfactants derived from commercial fluorochemicals:

2,2,3,4,4,4-hexafluorobutanol and perfluorobutyric acid.

Several synthetic routes are available to extend the hydrophobic chain of these two starting materials and to introduce the desired hydrophilic functionality required in surfactants. For example, 2,2,3,4,4,4-hexafluorobutanol may be reacted with a halogen acid such as 11-bromoundecanoic acid to yield the ester shown in Equation (I).

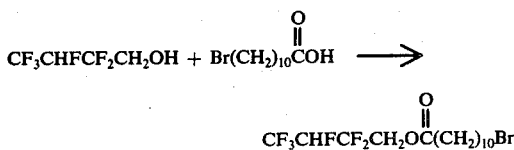

This ester may then be treated with pyridine to yield a cationic surfactant, the pyridinium bromide salt as shown in Equation (II).

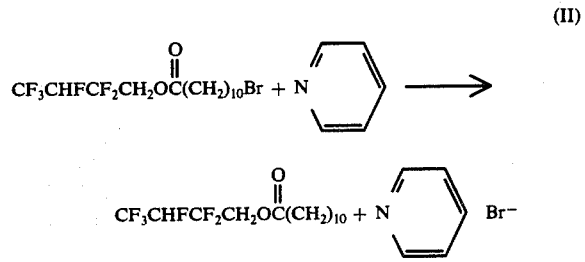

Perfluorobutyric acid may be esterified by reacting with methanol to obtain the ester shown in Reaction (III).

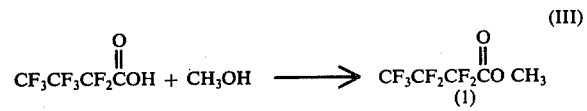

This ester may then be reacted with 3-dimethylaminopropylamine to give the amino-amide shown in Reaction (IV).

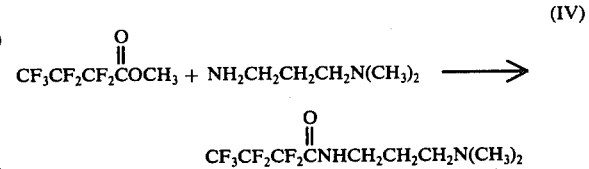

Reaction of the amino-amide from Reaction (IV) with hydrogen peroxide gives the N-oxide shown in Reaction (V).

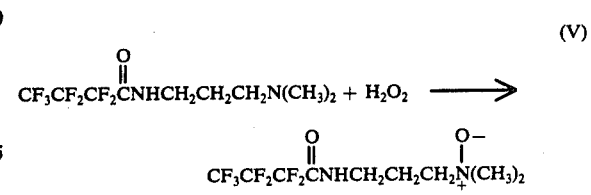

The N-oxide from Reaction (V) may be treated with glycolic acid to give a cationic surfactant, the salt shown in Reaction (VI).

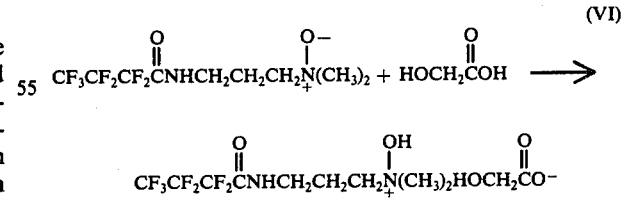

Equimolar or approximately equimolar quantities of reactants may be employed in Reaction (I) through (VI).

Antistatic properties of treated polymeric shapes such as fibers, filaments, foils or films containing from about 0.1% to about 5% by weight of one of the above surfactants based on the weight of the shape may be determined using the procedure described by M. J. Schick in Friction and Lubrication of Synthetic Fibers, Part I, Textile Research Journal, Vol. 43, No. 2, pp. 103–109 (February 1973). In this procedure, a given charge is placed on a polymeric shape such as a yarn specimen and the time required for one-half of the charge on the shape to dissipate from the shape is measured and recorded as the antistatic half-life.

Lubricity properties of shapes treated with one of the above surfactants may be determined by the procedure given in the above mentioned publication or by the procedure using the tripod sled apparatus as described by M. J. Schick, T. F. MacDonnell and J. H. Nash in Wear 25, (1973) pp 385–392. Both procedures are described in greater detail in the examples below.

The surfactant may be applied directly to the polymeric shape by any known method such as by means of a spray, by means of a bath, by means of an aqueous solution or dispersion or by means of a solvent such as a solution of the surfactant in a solvent such as chlorinated hydrocarbon, water or the like. If desired, the surfactant may be applied in solvent free form. Likewise, the surfactant may be compounded with the polymeric material prior to forming the filament, fiber, film, foil or the like. These application methods are well known in the art.

The surfactants of this invention may be used to treat various materials having any of the aforesaid shapes or structures, such materials include natural, man-made and synthetic fibers such as cotton, wool, silk, jute, sisal, hemp, fur, flax, kapok, rayon, cellulose acetate, cellulose triacetate, polyamides such as nylon, polyesters such as polyethylene terephthalate (Dacron), acrylics such as polyacrylonitrile, vinyl resins such as copolymers of polyvinyl chloride and polyvinyl acetate, copolymers of vinylidene chloride and vinyl chloride, copolymers of acrylonitrile and vinyl chloride, or the like, polystyrene, polyethylene, polypropylene, polyurethane, glass, ceramic, asbestos, protein fibers such as vicara and peanut protein, blends of these and the like. Blends of several fibers may be used.

The term fiber includes textile materials in the form of fibers, continuous or spun yarns, filaments, rovings, slivers, tops and the like.

For a fuller understanding of the nature and objects of this invention, reference may be made to the following examples which are given merely to illustrate the invention and are not to be construed in a limiting sense. All weights, proportions and percentages are on a weight basis unless otherwise indicated. Likewise, all temperatures are ° C unless otherwise indicated.

EXAMPLE I

This example describes the preparation of a pyridinium bromide salt of a bromo fluoro ester derived from 2,2,3,4,4,4-hexafluorobutanol and 11-bromoundecanoic acid.

2,2,3,4,4,4-Hexafluorobutyl 11-bromoundecylate

A 500 ml one-necked flask fitted with a Dean Stark trap was charged with 36.4 g (0.2 m) of 2,2,3,4,4,4-hexafluorobutanol, 53.0 g (0.2 m) of 11-bromoundecanoic acid, 0.5 g methane sulfonic acid and 100 ml of dry benzene. The reaction mixture was refluxed until the theoretical amount of water, 3.6 ml, was removed. The reaction mixture was washed with a 10% sodium carbonate solution. The benzene was removed under vacuum giving 2,2,3,4,4,4-hexafluorobutyl 11-bromoundecylate. IR analysis showed the following major absorption bands: 2930, 2860, 1760, 1190, 1110 cm$^{-1}$.

2,2,3,4,4,4-Hexafluorobutyl 11-pyridylundecylate bromide 2,2,3,4,4,4-hexafluorobutyl 11-bromoundecylate (21.5 g, 0.05 m) and 4.0 g (0.05 m) of pyridine were refluxed in 50 ml of anhydrous methanol for fifty-six hours. After vacuum stripping 25.4 g of 2,2,3,4,4,4-hexafluorobutyl 11-pyridylundecylate bromide designated as Product I (A) was obtained. IR analysis showed the following major absorption bands: 2930, 2860, 1755, 1635, 1490, 1190, 1105 cm$^{-1}$.

EXAMPLE II

This example describes the preparation of a fluorinated N-oxide and the corresponding N-oxide salt. The precursor of the N-oxide is derived from the reaction of methyl perfluorobutyrate and 3-dimethylaminopropylamine.

Methyl perfluorobutyrate

Perfluorobutyric acid (55 g, 0.26 m) in 25 ml of methanol containing 0.1 g of methane sulfonic acid was refluxed for 16 hours. The product was washed with a sodium carbonate solution and dried over magnesium carbonate. IR analysis showed the following major absorption bands: 2970, 1785, 1310, 1225, 1145, 1085 cm$^{-1}$.

N,N-dimethyl-N'-perfluorobutyrlamidopropyleneamine

Methyl perfluorobutyrate (38.4 g, 0.15 m), 3-dimethylaminopropylamine (15.5 g, 0.15 m) and 45 ml of isopropanol were refluxed for 3.5 hours. The solvent was removed under vacuum yielding 44.6 g of N,N-dimethyl-N'-perfluorobutyrlamidopropyleneamine. Amine nitrogen: calc. 3.35 meq/g; found 3.31 meq/g. IR analysis showed the following major absorption bands: 3310, 2950, 2870, 1710, 1220 cm$^{-1}$.

N-oxide of N,N-dimethyl-N'-perfluorobutyrlamidopropyleneamine

A 250 ml flask fitted with a stirrer, thermometer and addition funnel was charged with 32 g (0.1 m) of N,N-dimethyl-N'-perfluorobutyrlamidopropyleneamine and 35 ml of isopropanol. The solution was heated to 65° C and 10.8 g of 35% hydrogen peroxide solution was added. Following a slight exotherm, the reaction mixture was heated at 75° C for 5.5 hours. Titratable nitrogen in solution: calc. 1.44 meq/g; found 1.44 meq/g. IR analysis of an isolated sample designated as Product II (A) showed the following major absorption bands: 2950, 1695, 1210 cm$^{-1}$.

Glycolic acid salt of N-oxide of N,N-dimethyl-N'-perfluorobutyrlamidopropyleneamine A 25 g aliquot of the above product solution was neutralized with 2.7 g (0.036 m) of glycolic acid. Acid value found, 2.47 meq/g, titratable nitrogen found 2.45 meq/g. IR analysis of an isolated sample designated as Product II (B) showed the following major absorption bands: 3200, 3040, 2950, 1710, 1615, 1220 cm$^{-1}$.

EXAMPLE III

Lubricating properties of the above fluorochemical surfactants (Products of Example I (A) and II (B)) were determined using the following procedure. Coefficient of friction of each surfactant was measured using a Rothschild f-Meter 1081 for Measuring Coefficients of Friction (formerly Haberline, Inc., Raleigh, N.C., now Lawson-Hemphill Sales, Inc., Spartanburg, S.C.) with two Rothschild Electronic Tensiometers (formerly Haberline, Inc., Raleigh, N.C., now Lawson-Hemphill Sales, Inc., Spartanburg, S.C.), as described by M. J. Schick in Friction and Lubrication of Synthetic Fibers, Part I, Textile Research Journal, Vol. 43, No. 2, pp. 103–109 (February 1973). The surfactant was applied at 1% by weight based on the weight of fiber to the fiber and the treated fiber conditioned for 24 hours at 50% relative humidity and 72° F. The coefficient of friction of the conditioned fiber was then measured using the apparatus described in the following procedure.

An aqueous or isopropanol solution or dispersion of each surfactant was applied to a sample of 200/34 nylon filament yarn. Each yarn sample was then dried to remove water or alcohol and conditioned for 24 hours at 50% relative humidity and 72° F. The conditioned, treated, yarn sample, which contained 1% by weight of the surfactant based on the weight of the fiber, was then evaluated to determine the fiber to metal coefficient of friction at 50% relative humidity and 72° F. Coefficients of fiber to metal friction were measured using the Rothschild F-Meter 1081 with two Rothschild Electronic Tensiometers. Incoming tension on the yarn was 0.5 g per denier and the friction surface was a 0.5 inch diameter chrome pin having a roughness value of 52 RMS. Yarn was wrapped around the pin circumference once. Yarn speeds were: 5.5, 55, 100 and 300 yards per min. Results of these friction tests are shown in Table I below.

Antistatic properties of the conditioned, treated yarn samples were also determined. The antistatic half-life test used in these measurements is the test described in the above publication. In this test, a given charge is placed on a yarn specimen and the time required for one half of the charge on the specimen to dissipate from the test specimen is measured and recorded as the antistatic half-life of the treated fiber. Results of these tests are shown as the Antistatic Half-Life Seconds in Table I below. These results show the Products I (A) and II (B) exhibit a marked decrease in the antistatic half-life when compared to the results obtained with N-butyl stearate.

TABLE I

COEFFICIENTS OF FRICTION AND ANTI-STATIC PROPERTIES[1]

| Product | Speed (Yds/min) | Coefficient of fiber to metal friction | Anti-static Half-Life Seconds |
|---|---|---|---|
| Butyl Stearate | 5.5 | 0.160 | 36,000 |
|  | 55 | 0.160 |  |
|  | 100 | 0.173 |  |
|  | 300 | 0.186 |  |
| I (A) | 5.5 | 0.220 | 0.59 |
|  | 55 | 0.309 |  |
|  | 100 | 0.344 |  |
|  | 300 | 0.357 |  |
| II (B) | 5.5 | 0.383 | 19.35 |
|  | 55 | 0.430 |  |
|  | 100 | 0.459 |  |

TABLE I-continued

COEFFICIENTS OF FRICTION AND ANTI-STATIC PROPERTIES[1]

| Product | Speed (Yds/min) | Coefficient of fiber to metal friction | Anti-static Half-Life Seconds |
|---|---|---|---|
|  | 300 | 0.430 |  |

[1]1% nylon 200 Du Pont at 72° F, 50% humidity, 1 loop on chrome pin.

EXAMPLE IV

Each of the above fluorochemical surfactants (Products of Example I (A), II (A) and II (B)) was applied to the surface of nylon 66 film at a concentration of about 1% by weight of surfactant based on weight of the film. Each sample conditioned for one week at 50% relative humidity and 72° F prior to testing and then tested under these conditions. Frictional properties were determined by the procedure using the tripod sled apparatus described by M. J. Schick, T. F. MacDonnell and J. H. Nash in Wear 25, (1973) pp 385–392 to determine the coefficient of friction for film to metal boundary lubrication at a relative surface speed of 8 inches per minute and at three loads: 300 g, 600 g and 900 g. Frictional force was measured using a Statham Transducer (Statham Medical Instrument, Inc., Hato Rey, Puerto Rico) and recorded on a Sanborn Recorder 150 equipped with a carrier preamplifier (Hewlett Packard Co., Palo Alto, Calif.). The coefficient of friction, $f = F/W$ where $f$ signifies the frictional coefficient, $F$ the frictional force and $W$ the normal load, was then calculated from the average measured force divided by the load. A blank sample was also tested by the same procedure. Results of these test are shown in Table II.

TABLE II

COEFFICIENTS OF FRICTION (METAL-NYLON), TRIPOD SLED

| Product of Example | Coefficient of Friction | | |
|---|---|---|---|
|  | 300 gms. | 600 gms. | 900 gms. |
| Blank | 0.16 | 0.16 | 0.13 |
| I (A) | 0.003–0.03 | 0.03 | 0.05 |
| II (A) | 0.07 | 0.11 | 0.08 |
| II (B) | 0.07–0.13 | 0.03–0.18 | 0.07–0.15 |

While the invention has been described with reference to certain specific embodiments thereof, it is understood that it is not to be so limited since alterations and changes may be made therein which are within the full intended scope of the appended claims.

What is claimed is:

1. The cationic fluorochemical surfactant having the formula
   2,2,3,4,4,4-hexafluorobutyl 11-pyridylundecylate bromide.

2. The process of producing the surfactant of claim 1 comprising (a) reacting at reflux 2,2,3,4,4,4-hexafluorobutanol and 11-bromoundecanoic acid in presence of methane sulfonic acid as a catalyst and benzene as a solvent to obtain 2,2,3,4,4,4-hexafluorobutyl 11-bromoundecylate and then (b) reacting at reflux 2,2,3,4,4,4-hexafluorobutyl 11-bromoundecylate with pyridine in presence of methanol as a solvent to obtain 2,2,3,4,4,4-hexafluorobutyl 11-pyridylundecylate bromide.

3. The process of claim 2 comprising (a) reacting at reflux about 1 mole of 2,2,3,4,4,4-hexafluorobutanol and about 1 mole of 11-bromoundecanoic acid to obtain 2,2,3,4,4,4-hexafluorobutyl 11-bromoundecylate and then (b) reacting about 1 mole of 2,2,3,4,4,4-hexafluorobutyl 11-bromoundecylate with about 1 mole pyridine to obtain 2,2,3,4,4,4-hexafluorobutyl 11-pyridylundecylate bromide.

* * * * *